United States Patent

Duffy et al.

[11] Patent Number: 6,048,332
[45] Date of Patent: Apr. 11, 2000

[54] DIMPLED POROUS INFUSION BALLOON

[75] Inventors: Niall Duffy, Tuam; Micheal O'Loughlin, Milltown Malbay, both of Ireland

[73] Assignee: AVE Connaught, Dublin, Ireland

[21] Appl. No.: 09/169,340

[22] Filed: Oct. 9, 1998

[51] Int. Cl.[7] .................................................. A61M 29/00
[52] U.S. Cl. ...................... 604/96; 604/101; 604/104; 604/509; 604/536; 604/916
[58] Field of Search .................... 604/96, 97, 99, 604/101, 104, 912, 915, 917, 919, 500, 508, 509, 523, 536

[56] References Cited

U.S. PATENT DOCUMENTS

| | | |
|---|---|---|
| 797,676 | 8/1905 | Flowers . |
| 3,173,418 | 3/1965 | Baran . |
| 3,981,299 | 9/1976 | Murray . |
| 4,211,233 | 7/1980 | Lin . |
| 4,323,071 | 4/1982 | Simpson et al. . |
| 4,327,721 | 5/1982 | Goldin et al. . |
| 4,417,576 | 11/1983 | Baran . |
| 4,423,725 | 1/1984 | Baran et al. . |
| 4,437,856 | 3/1984 | Valli . |
| 4,578,061 | 3/1986 | Lemelson . |
| 4,636,195 | 1/1987 | Wolinsky . |
| 4,693,243 | 9/1987 | Buras . |
| 4,994,033 | 2/1991 | Shockey et al. . |
| 5,021,044 | 6/1991 | Sharkawy . |
| 5,049,132 | 9/1991 | Shaffer et al. . |
| 5,087,244 | 2/1992 | Wolinsky et al. . |
| 5,112,305 | 5/1992 | Barath et al. . |
| 5,213,576 | 5/1993 | Abiuso et al. . |
| 5,217,434 | 6/1993 | Arney . |
| 5,242,397 | 9/1993 | Barath et al. . |
| 5,254,089 | 10/1993 | Wang . |
| 5,279,565 | 1/1994 | Klein et al. . |
| 5,320,634 | 6/1994 | Vigil et al. . |
| 5,336,178 | 8/1994 | Kaplan et al. . |
| 5,354,279 | 10/1994 | Höfling . |
| 5,364,356 | 11/1994 | Höfling . |

(List continued on next page.)

FOREIGN PATENT DOCUMENTS

| | | |
|---|---|---|
| 0 383 429 A2 | 8/1990 | European Pat. Off. . |
| 0 753 322 A2 | 1/1997 | European Pat. Off. . |
| WO 92/10142 | 6/1992 | WIPO . |
| WO 97/02859 | 1/1997 | WIPO . |

*Primary Examiner*—Ronald Stright
*Assistant Examiner*—Jeremy Thissell
*Attorney, Agent, or Firm*—Sterne, Kessler, Goldstein & Fox PLLC

[57] ABSTRACT

The systems and methods described herein include drug delivery catheters that have dimpled porous balloons mounted onto the distal end of the catheter. In one embodiment, the balloons are adapted for delivering therapeutic agents to the tissue wall of a body lumen, and to this end include a plurality of dimples formed in the exterior surface of the balloon, with each dimple having at least one aperture through which a fluid delivered into the interior of the balloon can extravasate. It is understood that the balloons described herein provide, inter alia, increased coverage of the tissue wall to which the agent is being delivered and less traumatic contact between the agent being delivered and the tissue wall.

16 Claims, 5 Drawing Sheets

U.S. PATENT DOCUMENTS

| | | |
|---|---|---|
| 5,370,614 | 12/1994 | Amundson et al. . |
| 5,389,314 | 2/1995 | Wang . |
| 5,415,637 | 5/1995 | Khosravi . |
| 5,419,777 | 5/1995 | Höfling . |
| 5,464,395 | 11/1995 | Faxon et al. . |
| 5,554,114 | 9/1996 | Wallace et al. . |
| 5,554,119 | 9/1996 | Harrison et al. . |
| 5,558,642 | 9/1996 | Schweich, Jr. et al. . |
| 5,569,198 | 10/1996 | Racchini . |
| 5,599,306 | 2/1997 | Klein et al. . |
| 5,609,574 | 3/1997 | Kaplan et al. . |
| 5,611,775 | 3/1997 | Machold et al. . |
| 5,653,689 | 8/1997 | Buelna et al. . |
| 5,674,287 | 10/1997 | Slepian et al. . |
| 5,681,281 | 10/1997 | Vigil et al. . |
| 5,693,029 | 12/1997 | Leonhardt . |
| 5,709,874 | 1/1998 | Hanson et al. . |
| 5,713,860 | 2/1998 | Kaplan et al. . |
| 5,713,863 | 2/1998 | Vigil et al. . |
| 5,716,340 | 2/1998 | Schweich, Jr. et al. . |
| 5,746,716 | 5/1998 | Vigil et al. . |
| 5,772,629 | 6/1998 | Kaplan . |
| 5,873,852 | 2/1999 | Vigil et al. . |

DIMPLED POROUS INFUSION BALLOON

FIELD OF THE INVENTION

This invention relates generally to the medical field of atherosclerotic lesion treatment. Specifically, a device is disclosed that allows the localized administration of various therapeutic agents to the inner wall of an involved vessel. In one practice, the devices described herein are employed to prevent or reduce post angioplasty vascular restenosis precipitated by either reoccurrence of the initial thrombotic lesion or by hyperplasia of local vessel cellular components.

BACKGROUND OF THE INVENTION

Percutaneous transluminal angioplasty (PTA) has attained significant success in the treatment of discrete atherosclerotic lesions in the coronary and non-coronary vasculature. This procedure involves percutaneously introducing a specially constructed catheter equipped with a balloon on the distal shaft into the vasculature, guiding the catheter system to an area of vascular stenosis and inflating the balloon to effect a dilatation of the stenotic area. The techniques of PTA, well known in the arts of interventional cardiology and interventional radiology, provides effective alternatives to the more invasive surgical methods of vascular reconstruction and bypass. More recently, PTA has been complemented by other endovascular procedures that allow diagnosis and treatment of vascular lesions. Examples of these endovascular procedures include atherectomy, intraluminal stenting and grafting, thromboembolectomy, angioscopy and endovascular ultrasonography. Major endovascular methods for treating a vascular stenosis include balloon dilatation, debulking or excising plaque, and providing an intraluminal scaffold or stent.

A comprehensive mechanism for a successful angioplasty has been proposed whereby the atherosclerotic intima is ruptured and partially dehisced, thereby freeing the media from the adherent restraint of the atherosclerotic plaque and allowing the media to become overstretched. (WR Castenada-Zuniga et al.: The mechanism of balloon angioplasty, Radiology 135:565–571, 1980) The overstretching distends the media and results in some injury to its elastic elements and muscle fibers. Blood flow in the lumen keeps the media distended as it heals by collagen deposition. The vessel thus reforms in its new configuration, resulting in a permanent widening of the vessel lumen. Balloon angioplasty results in extensive injury to all layers of the vessel wall, including plaque fracture, media stretch, dissection and rupture, and adventitial stretch with focal ruptures in adventitial collagen. Healing of these lesions takes place at all levels, requiring full-thickness repair of the arterial wall. Postulated repair mechanisms within the media and the adventitial include sequences of inflammation, neovascularization, fibroblast proliferation and eventual collagen deposition.

Much research interest has focused on the changes that occur in the intimal layer following angioplasty. The intima is generally considered to consist of a single layer of endothelial cells and a thin basal lamina. Successful PTA involves interruption of the intimal layer of the vessel, thus violating the impermeable barrier that the intima provides between the blood flowing within the vessel lumen and the deeper layers of the vessel itself. Endovascular surgery can induce similar trauma. Under normal conditions, the healthy intima allows for smooth blood flow within the vascular channel and minimizes the risk of triggering intravascular thrombosis. In its normal state, the smooth layer of endothelial cells comprising the intima is actively antithrombotic. Vessels with altered endothelial coverage are at increased risk for intravascular thrombosis. Restoration of intimal integrity is therefore a paramount concern for unimpeded blood flow.

Early complications of PTA reflect the acute, full-thickness injury to the vessel wall that the procedure entails. These complications, including plaque dissection and thrombosis, can result in an abrupt closure of the vessel that has undergone PTA. Early reocclusion of a recanalized vessel is commonly due to thrombus formation, a process set in motion by the vascular injury associated with the endoluminal manipulation. Endothelial injury associated with PTA triggers the coagulation cascade which results in thrombin production. Thrombin, in turn, has many related actions, including the production of fibrin and the activation of platelets. Fibrin and platelets join together within the vessel to form a thrombus. The thrombus then obstructs the blood vessel partially or completely. Abrupt closure of a vessel causes acute ischemia in the perfused tissues. In the coronary circulation, abrupt closure can cause myocardial infarction or death if blood flow is not emergently restored.

The later onset of vessel occlusion following endovascular intervention is termed restenosis. Restenosis can occur following any endovascular treatment of a stenotic condition. Restenosis has been well-studied following PTA. Approximately one-third of PTA patients require a second or third therapeutic intervention due to restenosis. The etiology of this condition following PTA involves mechanisms of vascular healing following the trauma induced by this procedure.

The intima damaged by endovascular procedures heals by re-endothelialization and neointimal formation. Intimal repair, however, involves not only the endothelial cells but also the cells of the media. One striking characteristic of the normal healthy vessel wall is the slow growth rate of both the intimal endothelial cells and the smooth muscle cells (SMCs) of the media. Damage to the vascular endothelium is understood to trigger a complex series of events by which these cells undergo a transformation from their normal resting state to a state of heightened biological activity.

In response to vessel wall injury, SMCs undergo a series of distinct changes, the earliest of which is replication. This is followed by migration from the media across the internal elastic lamina into the intima. Once in the intima, the SMCs proliferate and ultimately synthesize and secrete extracellular matrix. This cellular proliferation, as well as the deposition of connective tissue elements, forms the basis of the observed intimal changes in the lumen of a traumatized vessel. Some investigators prefer to call these phenomena myointimal hyperplasia rather than intimal hyperplasia to underscore the role of the medial smooth muscle cell.

The biological complexity of these acute and longer-term events has inspired investigators to consider pharmacological means for their manipulation in order to preserve the beneficial effects of endovascular procedures. For example, regulation of SMC hyperplasia may affect rates of restenosis. Since SMCs are understood to dedifferentiate from a contractile to a synthetic phenotype, followed by intense proliferation and the production of connective tissue, one method of combating restenosis might be the administration of various therapeutic agents known to block these processes. Additional therapeutic interventions could modulate the inflammatory processes or the thrombotic processes, both of which have been implicated in abrupt occlusion or restenosis.

Delivering the therapeutic agents to these target tissues poses problems, however. Systemically administered drugs such as anticoagulants, vasodilators, etc., have proven ineffective in preventing restenosis. Furthermore, conventional methods of systemic drug delivery produce blood levels that may have dangerous side-effects. Finally, there is an inevitable fluctuation of serum drug concentrations following systemic administration, providing inconstant levels of the active agent available to the target tissues.

Local intramural therapy may also be applied to non-arterial luminal structures including the prostate via the prostatic urethra, the fallopian tubes, the ureters and the gastrointestinal tract. Local administration of therapeutic agents to vascular tissues following PTA and related endovascular procedures has been proposed using a variety of systems. General problems with local administration include difficulties with retaining the agent in the vicinity of the lesion and risks of further injuring the vessel wall following endovascular trauma. A successful device must both provide adequate concentration of therapeutic agent to the treatment area and must also avoid further trauma to the already damaged vessel wall. No such device yet exists in the art.

Several devices have been disclosed which place the treatment apparatus containing the therapeutic agent in contact with the vessel wall at the site to be treated and simply release the agent onto the vessel wall. (See U.S. Pat. No. 5,087,244, issued to Wolinsky et al., U.S. Pat. No. 5,242,158, issued to Arney, U.S. Pat. No. 5,389,314, issued to Wang, and U.S. Pat. No. 5,213,576, issued to Abiuso et al.) With these systems, the agent is placed in contact with the treatment area but is mostly washed away by the bloodstream, resulting in unnecessary distal dissemination, inadequate local perfusion or both. Further, the infusion process can create a forceful stream of fluid exiting from the treatment apparatus that directly impinges upon the vessel wall. If high pressure is used during inflation, the fluid may be forced through the perforations in an infusion balloon at a high velocity, with resultant damage to the local tissue. This contact, termed "jetting" can extend the zone of injury produced by the PTA. Examples of the damage that can result from jetting include direct cellular injury, edema formation and vessel wall rupture. The vascular damage due to jetting can exacerbate the processes that lead to the development of intimal hyperplasia and ultimately result in restenosis.

Other devices exist that propose a direct application or injection of the drug to a segment of the vessel wall so that the drug penetrates into the deeper layers. U.S. Pat. No. 5,112,305, issued to Barath et al., teaches a method of treatment of an atherosclerotic blood vessel that delivers a therapeutic agent to the blood vessel wall through a rapid bolus of a therapeutic agent into tubular extensions of the balloon. This system, though, can produce increased damage to an already traumatized area with uncontrolled risk of endothelial and medial injury. Further, there is an imprecise application of the therapeutic agent, with risk of its loss downstream. U.S. Pat. No. 5,354,279, issued to Hofling, discloses a system of needle injectors that penetrate the vessel wall for direct application of a therapeutic agent within the wall. However, there is no calibration system to determine the depth of the needles, and the injectors themselves may further traumatize the wall of the moving vessel. U.S. Pat. No. 5,693,029, issued to Leonhardt, discloses a catheter system designed to overcome the rigidity of the Hofling catheter and to puncture the vessel wall to a controlled depth, but does not avoid mechanical wall trauma. U.S. Pat. No. 5,611,775, issued to Machold, discloses a catheter with multiple apertures designed to inject fluid into the tissue wall under pressure, thus again possibly producing further vessel wall injury.

There therefore remains in the art an unmet need for a system that provides controlled local delivery of a therapeutic agent to the vessel wall but that avoids the dangers of extending the local injury resulting from endovascular procedures. The availability of a drug delivery system that achieves these two goals would permit more successful manipulation of the biological environment within the blood vessel wall. Intervening in the biological processes of vessel wall healing can in turn reduce the incidence of restenosis following PTA and other endoluminal procedures for vascular disease, thereby resulting in more durable clinical benefits.

SUMMARY OF THE INVENTION

The systems and methods described herein include drug delivery catheters that have a dimpled porous balloon mounted onto the distal end of the catheter. In one embodiment, the balloon is adapted for delivering a therapeutic agent to the tissue wall of a body lumen. To this end, the systems and methods described herein include at least one dimple formed in the exterior surface of the balloon, with the dimple having at least one aperture through which a fluid delivered into the interior of the balloon can extravasate. It is understood that the balloon described herein provides, inter alia, increased coverage of the tissue wall to which the agent is being delivered.

More specifically, the systems and methods described herein can deliver a fluid vehicle carrying a therapeutic agent to an interior surface of a body lumen. The term fluid vehicle as employed herein can include any solvent physiologically compatible with the human body in which a therapeutic agent can be dissolved, suspended or otherwise carried. Examples of fluid vehicles include liquids, gels and emulsions. The term therapeutic agent as employed herein can be understood to be any substance, or precursor to a substance, that has a pharmacological effect upon the human body, including but not limited to drugs, hormones, peptides or other biologically active entities such as microorganisms and vectors carrying modified genetic material.

The fluid vehicle containing the therapeutic agent passes through the catheter system to contact the inner or luminal surface of the structure within which the catheter has been positioned. While the fluid vehicle is understood to contact the inner surface of the body lumen, and deliver the therapeutic agent to this surface, the action of the therapeutic agent is not limited to what it may accomplish by contacting this surface. Rather, it is understood that various therapeutic agents will penetrate the inner surface of the body lumen to enter the tissues deep to the inner surface and exert therapeutic effects thereupon. Moreover, it is understood that the agents may be carried to other locations within the body, to provide treatment to areas larger than or distant from the areas of tissue contact. The efficacy of the therapeutic agent delivered by this system is thus not limited to its topical effects upon the inner surface of the body lumen. The systems described herein can deliver one therapeutic agent or more than one therapeutic agent, in keeping with the clinical needs of the patient. It is understood that each therapeutic agent may exert its own effect upon a particular tissue, whether superficial or deep to the point of application. It is further understood that more than one therapeutic agent may interact to produce a single set of therapeutic effects, as for example when one agent serves to activate or potentiate the other upon contact with a particular tissue.

The catheter systems and methods described herein can be adapted for insertion into any body lumen, including but not limited to the lumen of a blood vessel, a cardiac chamber or a hollow viscus. The proximal portion of the catheter can be disposed outside the patient's body and can be manipulated by the clinician. The distal portion can be positioned in the vicinity of the tissues that will be treated by these systems and methods. There is at least one lumen through the catheter. A catheter lumen is a channel within a catheter shaft that permits the introduction and passage of fluids. At least one lumen of the catheter is in fluid communication with the interior of a medication-dispensing balloon mounted on the distal portion of the catheter. A single-lumen catheter provides a single conduit for inflating a medication-delivering balloon and for dispensing the fluid vehicle carrying the therapeutic agent. A multilumen catheter also falls within the scope of the disclosed systems and methods; a multilumen catheter can provide one lumen for inflating the balloon and another lumen for dispensing the fluid vehicle carrying the therapeutic agent. Additional lumens can be added within the catheter to allow a plurality of therapeutic interventions. For example, the catheter may include a medication lumen that enables the catheter to deliver medications at a site proximal or distal to the balloon apparatus, an additional lumen that allows the balloon to deliver medications, and a separate conduit for inflating the medication-delivering balloon or another balloon disposed on the catheter shaft. Multiple conduits can be preferentially arranged so that they are not in fluid communication with each other. An array of conduits can be connected to a manifold at the proximal portion of the catheter through which the clinician can control the therapeutic interventions.

The medication-delivering balloon bears at least one concavity upon its wall within which is disposed at least one aperture through which the fluid vehicle carrying the therapeutic agent exits the lumen of the balloon to contact the interior surface of the body lumen. A concavity, as the term is used herein, means a depression that deforms the balloon wall in a concave direction. Disposed within the wall of the balloon can be one or more than one concavity, with the term "plurality" understood to mean more than one. In one embodiment, one aperture is located within one concavity. However, a plurality of apertures can be positioned within one concavity without departing from the scope of the invention. Further, it is understood that more than one aperture-bearing concavity can be disposed upon the wall of the balloon. Herein, the term "a concavity" is understood to include at least one concavity. Further, it is understood that more than one aperture can be disposed upon the wall of the balloon. An aperture can be positioned within a concavity or upon the non-concavity bearing part of the balloon wall. Herein, the term "an aperture" is understood to include at least one aperture. A variety of combinations of apertures and concavities can be employed with the systems disclosed herein. In one embodiment, there is a plurality of concavities arranged on the balloon wall in a regular pattern with all concavities bearing a single aperture and with all apertures located within a concavity. This arrangement permits substantially uniform distribution of the therapeutic agent circumferentially, and allows substantially uniform stream velocity in all areas where the fluid vehicle contacts the inner luminal wall. Variations in these arrangements can be undertaken to achieve different therapeutic goals. For example, a balloon bearing concavities on only one portion can be directed to the treatment of an asymmetrical lesion within the body lumen. Other variations of the systems and methods disclosed herein will be apparent to those of ordinary skill in the art.

Combined with the local delivery of the therapeutic agent can be the dilatation of a stenotic area of a body lumen. The term stenosis is used to designate any segment of a luminal structure where the diameter of the lumen is less than normal, whereby the physiological functioning of the luminal structure is adversely affected. Techniques for dilatation include those that expand the stenotic area to a more normal dimension. These techniques include, for example, stretching techniques like balloon dilatation. Other techniques directed from within the lumen to open the narrowed segment of a stenotic lumen are also encompassed by the term dilatation as used herein. Such techniques would include the partial or complete endoluminal excision of lesions impinging upon the lumen that decrease its cross-sectional area.

Without departing from the scope of the systems and methods described herein, the drug-delivery balloon can be disposed on the distal end of the catheter surrounding and external to an inner balloon or a plurality of inner balloons. These additional balloons permit the catheter system to carry out a variety of therapeutic functions, including drug delivery, dilatation of stenoses, or other therapeutic functions that may be clinically indicated.

The method for applying the therapeutic agent to the body lumen includes a set of techniques performed by a clinician. First, the clinician gains access to the body lumen, using standard procedures. A blood vessel, for example, can be entered either percutaneously or by cutdown. Once the catheter has entered the body lumen, it is then directed through the course of the body lumen to be positioned at the site to be treated. The medication-delivering balloon is inflated until it contacts the interior surface of the body lumen. The clinician then directs the fluid vehicle containing the therapeutic agent through the catheter to the interior lumen of the medication-delivering balloon. The flow rate by which the fluid vehicle extravasates through the apertures in the balloon wall is selected by the clinician so as to provide an optimal level of the therapeutic agent at the treatment site. In one embodiment, the clinician can control flow rate of the fluid vehicle. In another embodiment, the clinician can control perfusion pressure of the fluid vehicle. In yet another embodiment, the clinician can control both these variables. Different therapeutic agents have different onsets of action, durations of action and dispersion properties, so no specifications can be recited delimiting the quantity of therapeutic agent delivered through these systems and methods. Rather, these parameters are to be selected by the clinician based on an understanding of the inherent characteristics of the agent involved and of the therapeutic effects to be achieved. These understandings are familiar to those of ordinary skill in the relevant arts. The scope of this invention is intended, therefore, to extend to the plurality of therapeutic applications envisioned by these practitioners.

The many other objects, features and advantages of the present invention will become apparent from the following description. A more comprehensive understanding of the systems and methods described herein will be evident after reviewing the forthcoming diagrammatic representations and their detailed descriptions.

BRIEF DESCRIPTION OF THE DRAWINGS

The foregoing and other objects and advantages of the invention will be appreciated more fully from the following description thereof, with reference to the accompanying drawings wherein:

FIG. 2a is a cross-sectional view of an embodiment of the balloon as seen along the line 24–24' in FIG. 1;

FIG. 2b is a cross-sectional view of the catheter shaft in FIG. 2a as seen along the line A–A' in FIG. 2a;

FIG. 5b is a cross-sectional view of the concavity depicted in FIG. 5a;

FIG. 7a is a cross-sectional view of a dimpled porous balloon disposed surrounding a second balloon disposed on the distal end of the catheter;

FIG. 7b is a cross-sectional view of the catheter shaft in FIG. 7a as seen along the line B–B' in FIG. 7a;

DETAILED DESCRIPTION OF THE ILLUSTRATED EMBODIMENTS

To provide an overall understanding of the invention, certain illustrative embodiments will now be described, including a dimpled porous drug delivery balloon. However, it will be understood by one of ordinary skill in the art that the dimpled porous drug delivery balloon systems described herein are merely illustrative of the invention, and that other systems and methods can include the teachings discussed herein. Furthermore, it will be understood that the systems described herein can be adapted and modified without departing from the scope thereof.

Figure 1:
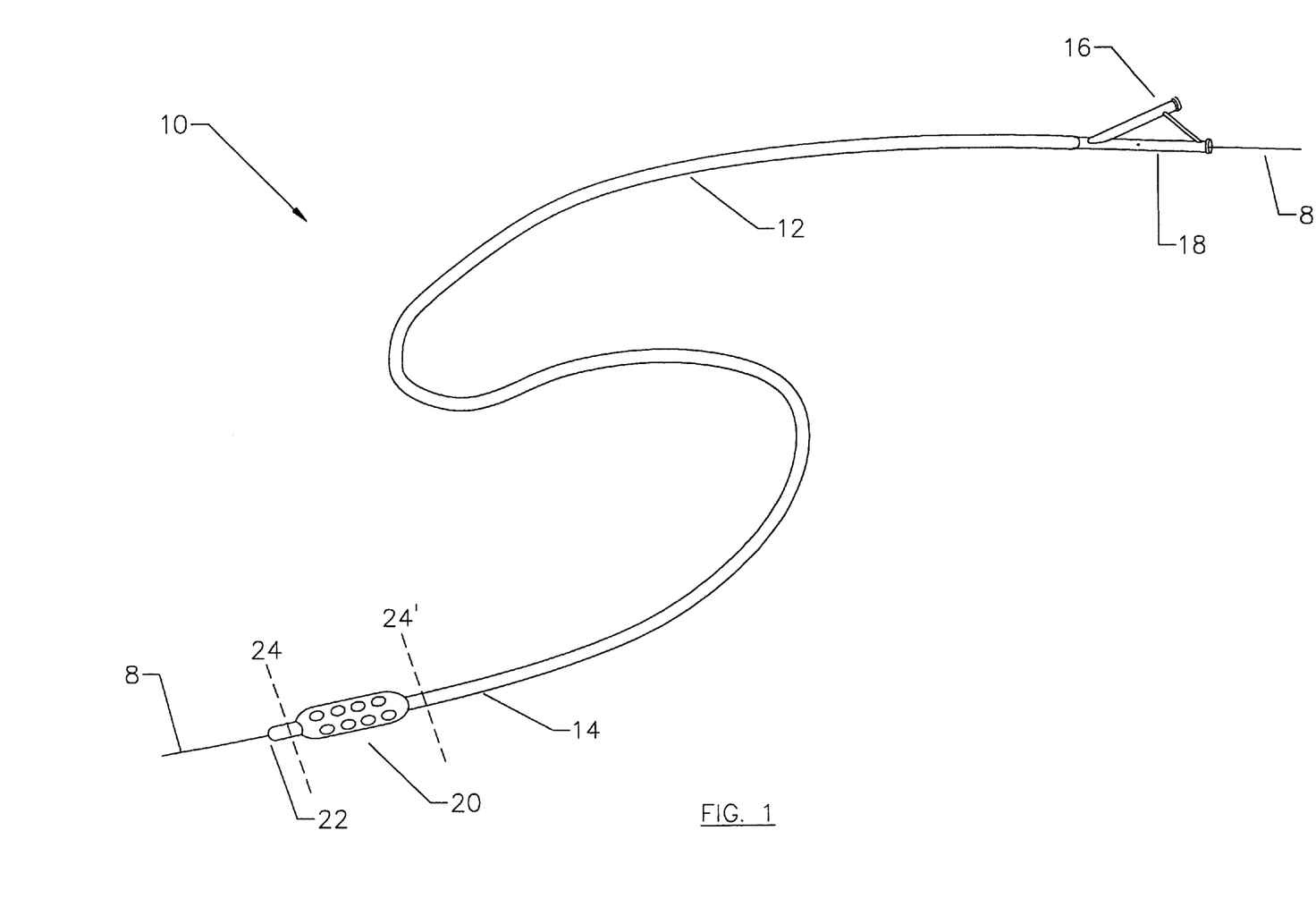
FIG. 1 illustrates a catheter with a dimpled porous balloon disposed at its distal end.

The embodiment depicted in FIG. 1 incorporates a catheter 10 that is adapted for disposal within a body lumen or cavity in a manner well-known to practitioners in the art. The catheter 10 in this embodiment has a proximal portion 12 attached to a catheter hub 18 that allows the clinician to manipulate the catheter 10. The catheter hub 18 can include an infusion port 16 through which fluids can be introduced into the catheter 10. These fluids can include fluids used to inflate the balloon and fluids used as vehicles for therapeutic agents. The injector port 16 can include a manifold system that contains multiple lumens for the introduction of fluids. The lumen in the injector port 16 is in fluid communication with the catheter lumen. The catheter 10 is dimensionally adapted for insertion into a particular body lumen or cavity. In one practice, the catheter is passed into the body lumen over a guidewire 8. The guidewire 8 is adapted in length to reach the site of the endoluminal lesion to be treated. Guidewire 8 lengths can range from 145 cm to 260 cm. Catheter 10 length similarly varies, ranging from approximately 65 to 140 cm., depending upon the targeted anatomic site. Guidewire 8 diameters vary, depending upon the clinical indication. In one embodiment, the guidewire diameter is approximately 0.014". In the embodiment illustrated in FIG. 1 a balloon 20 is shown mounted upon the distal portion 14 of the catheter proximal to the tip 22. A guidewire 8 is shown passing through the catheter hub 18, through the catheter lumen and exiting the catheter tip 22. In one embodiment, a separate channel can be disposed within the catheter lumen to allow passage of the guidewire 8. It is understood that the balloon 20 of this catheter system can be adapted for use with alternative types of catheters 10, including, for example, the rapid exchange catheter.

The balloon 20 in this Figure is shown in an inflated position. The balloon 20 can be inflated after it is positioned at a treatment site within a body lumen. Pre-inflating the balloon 20 increases its profile and makes it more difficult to direct to the treatment area. Although only one balloon is depicted in this embodiment, it is understood that alternative embodiments can be fabricated that incorporate additional balloons disposed internal to the dimpled porous balloon, proximal to the dimpled porous balloon or distal to the dimpled porous balloon. These alternative embodiments with combinations of balloons can be constructed by those of ordinary skill in the art without departing from the scope of the systems and methods described herein.

Figures 2A, 2B:
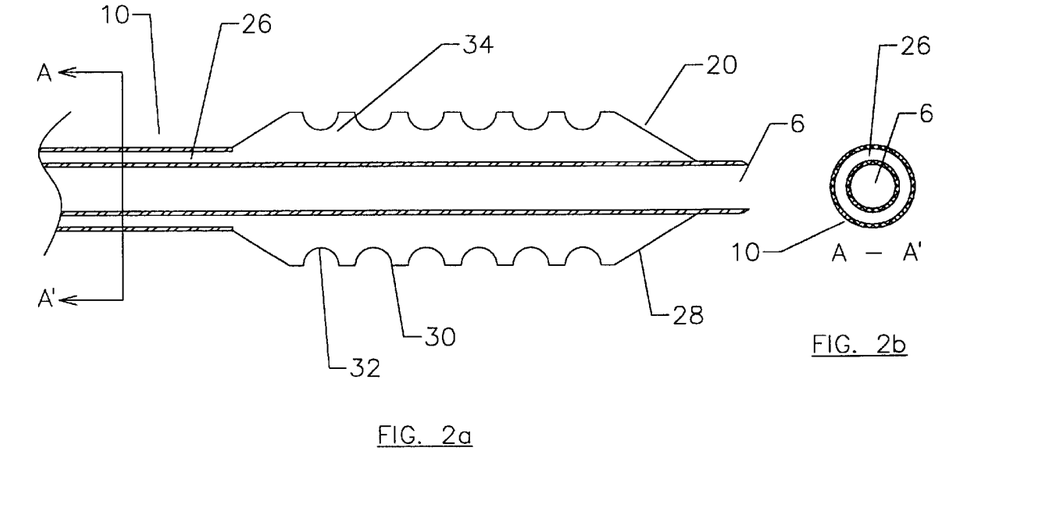

FIG. 2a shows a longitudinal cross-sectional view of the balloon 20 taken along the line 24–24' in FIG. 1. This figure shows in more detail the relationship of the balloon 20 to the catheter 10 upon which it is disposed. The catheter lumen 26 is in fluid communication with the interior 34 of the balloon 10. In the illustrated embodiment, fluid passes from the interior of the catheter lumen 26 into the interior 34 of the balloon 10. In the embodiment depicted in this figure, the introduction of fluid into the balloon interior 34 permits inflation of the balloon 20 and further permits extravasation of said fluid through apertures 32 in the balloon wall 28. As depicted in this Figure, the fluid within the balloon 20 is ejected through the aperture 32 in the balloon wall 28 into the interiority of the concavity 30 at a pressure related to the pressure within the balloon interior 34. This figure shows a guidewire channel 6 disposed interior to the lumen 26 in fluid communication with the interior 34 of the balloon. In an alternative embodiment, a separate lumen can be disposed within the catheter 10 to permit inflation of the balloon 20 while yet another lumen within the catheter 10 permits the introduction of the fluid vehicle bearing the therapeutic agent into the balloon interior 34. These additional lumens can accompany the guidewire channel 6 within the catheter 10 shaft. In the illustrated embodiment, the apertures 32 are shown to be recessed within a plurality of concavities 30 formed by deformations in the balloon wall 28. Balloon 20 lengths are selected to conform to the dimensions of the lesion being treated. Lengths of 2 and 4 cm. are available in some embodiments, although other lengths can also be suitable for certain therapeutic indications. Selection of balloon 20 length is a practice familiar to those of ordinary skill in these arts. The balloon wall 28 can be formed from materials well-known in the art, including for example polyethylene terphthalate.

FIG. 2b shows a cross-sectional view of the catheter 10 taken along line A–A'. This figure depicts in more detail one arrangement of the guidewire channel 6 and the lumen 26 in fluid communication with the interior of the balloon within the catheter 10 shaft. In the illustrated embodiment, the guidewire channel 6 is disposed coaxially with and interior to the lumen 26 that is in fluid communication with the interior of the balloon. Alternative arrangements of these two lumens can be envisioned without departing from the scope of the systems and methods described herein. Furthermore, additional lumens can be provided within the catheter 10 shaft and arrayed in various orders with respect to the lumens illustrated in this figure.

Figure 3:
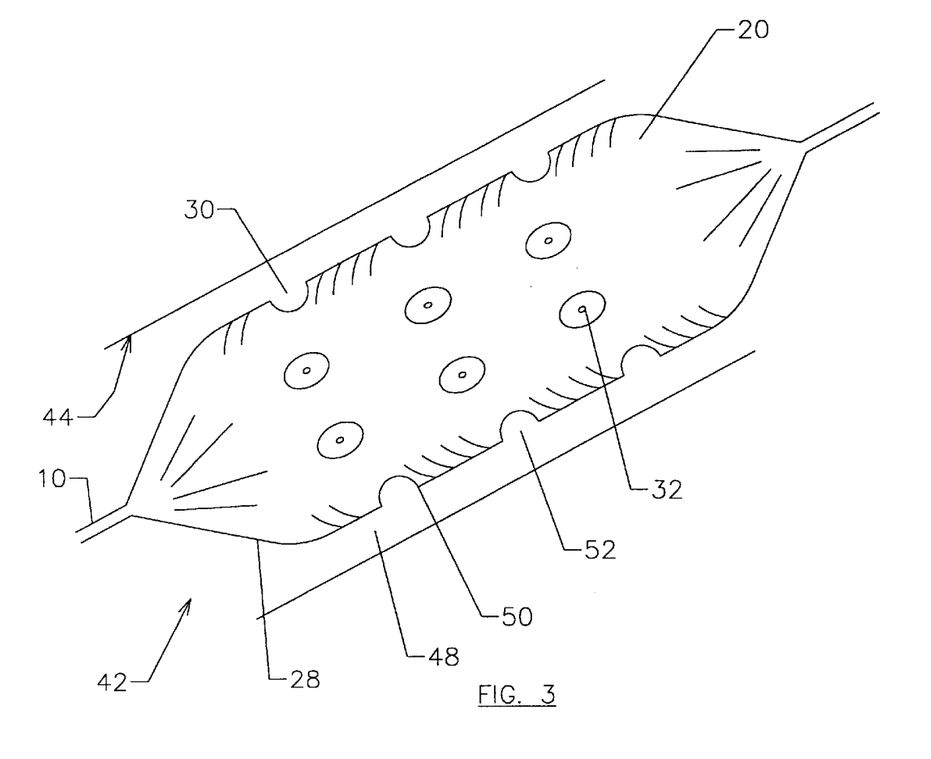
FIG. 3 is a perspective view of the balloon of the catheter depicted in FIG. 1 positioned within a body lumen.

FIG. 3 depicts a perspective view of an embodiment of a catheter 10 disposed within a body lumen 42. One embodiment of the systems disclosed herein is a catheter 10 dimensionally adapted for positioning within a blood vessel;

however, the catheter 10 according to these systems can be introduced into any body lumen 42 and is not limited to intravascular use. The catheter 10 bears a balloon 20, shown in this Figure in an inflated state. The balloon 20 is inflated sufficiently to permit its wall 28 to attain direct contact 48 with the interior surface 44 of the body lumen 42. In the illustrated embodiment, the concavities 30 in the balloon wall 28 retain their indented configuration as the balloon is inflated. The edges 50 of the concavities 30 are in contact with the interior surface 44 of the body lumen 42. The open face 52 of the concavity 30 provides a surface area for contact between the contents of the concavity 30 and the interior surface 44 of the body lumen 42. The concavity 30 can be a fixed depression deforming the balloon wall 28 that retains a concave shape as the balloon 20 is inflated until the balloon wall 28 contacts the interior surface 44 of the body lumen. In the embodiment depicted in FIG. 3, an aperture 32 is shown to be located within a concavity 30. The concavity 30 distances the aperture 32 it contains from the interior surface 44 of the body lumen 42. The distance provided between the aperture 32 and the interior surface 44 of the body lumen 42 defines a space by which the aperture 32 is removed from the tissue wall. By increasing the distance between the aperture 32 through which the fluid vehicle exits the balloon 20 and the interior surface 44 of the body lumen 42 that the fluid vehicle strikes, the concavity 30 serves to reduce the velocity of this fluid stream and thus to reduce the physiologically detrimental effects of this contact. The systems and methods described herein can thereby diminish the damage caused by the jetting effects of the fluid striking the interior surface 44 of the body lumen 42 at excessive velocities. The concavity 30 further provides a site for collection of a volume of fluid vehicle bearing the therapeutic agent, thereby increasing the surface area over which this fluid contacts the interior surface 44 of the body lumen 42.

The shape of the concavity 30 can be selected to attain particular physiological goals. A deeper concavity 30 will increase the distance between the aperture 32 and the interior surface 44 of the body lumen 42. A wider concavity 30 will allow more surface area for contact between the therapeutic agent and the interior surface 44 of the body lumen 42. The geometry of the concavity 30 can be correlated with the elastic characteristics of the balloon wall 28 so that the concavity 30 retains an advantageous shape upon balloon expansion. In one embodiment, the concavity 30 comprises a segment of a sphere. Practitioners skilled in the art can form concavities 30 in other shapes, for example ovals or irregular curvilinear depressions, without departing from the scope of the invention. The concavity 30 can retain its shape when subjected to pressure from within the balloon 20.

Figure 4:
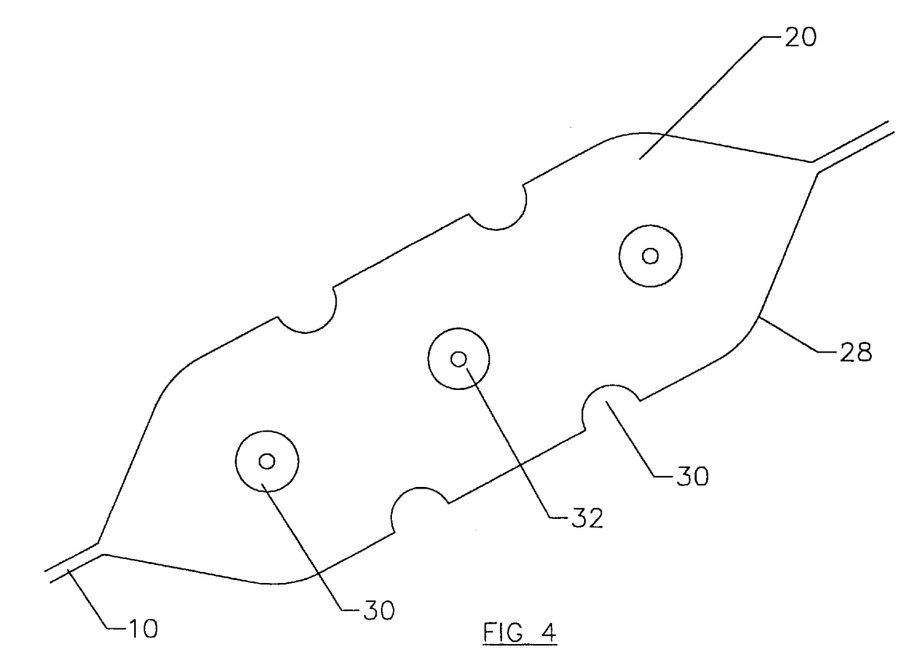
FIG. 4 depicts in more detail the balloon of FIG. 1.

FIG. 4 shows in more detail an embodiment of the balloon 20 in its inflated state. In this embodiment, the balloon 20 is mounted upon the catheter 10. This figure shows the concavities 30 in the balloon wall 28 dispersed symmetrically across the surface of the balloon 20. However, this symmetrical arrangement is one of a plurality of arrays of concavities 30 that fall within the scope of the disclosed systems and methods. This figure illustrates several concavities 30 seen in cross-section and seen en face. In this embodiment, an aperture 32 is shown to be positioned at the base of each concavity 30, although alternate positioning of one or several apertures 32 within a concavity 30 fall within the scope of the disclosed systems. The aperture 32 is of a dimension to provide delivery of selected volume of the fluid vehicle to the surface being treated. Aperture 32 dimensions can be selected in accordance with desired flow rates and desired fluid stream velocity. The position of the aperture 32 within the concavity 30 can be at the base, but other locations can be selected without departing from the scope of the systems disclosed herein. The term "base" refers to the deepest recess of the concavity 30. In a concavity 30 shaped substantially as a segment of a sphere, this basal location of the aperture 32 will distance it maximally from the surface being treated. In one embodiment, each concavity 30 contains at least one aperture 32. In another embodiment, each concavity 30 contains only one aperture 32, and each aperture 32 is located within a concavity 30 substantially at its base.

Figure 5A:
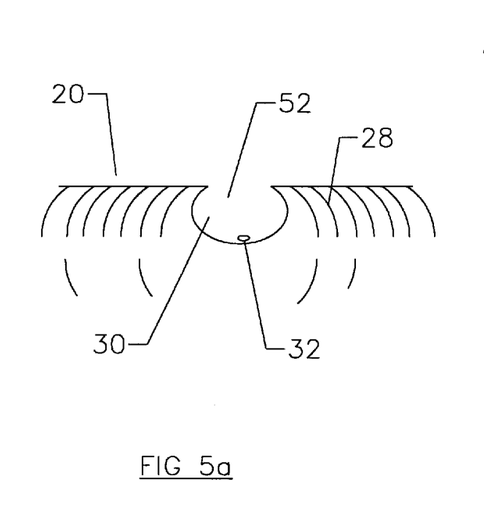
FIG. 5a is a perspective view of a concavity in the balloon of FIG. 1.
Figure 5B:
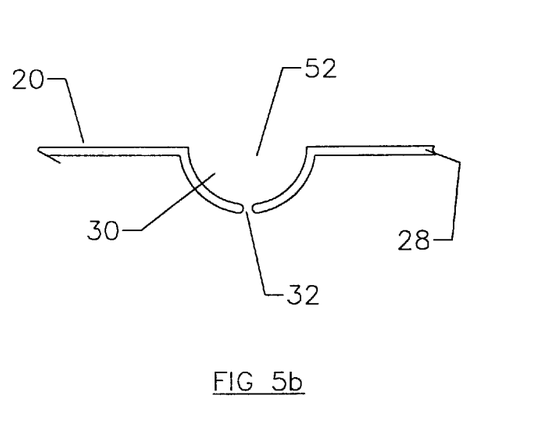

FIG. 5a shows in more detail a perspective view of a concavity 30 indenting the wall 28 of the balloon 20. FIG. 5b shows in more detail a cross-sectional view of an concavity 30 indenting the wall 28 of the balloon 20. The aperture 32 in this embodiment is located substantially at the base of the concavity 32. FIG. 5b shows a cross-sectional view of an embodiment of a concavity indenting the balloon wall 28. The shape of the concavity 30 substantially resembles a segment of a sphere. The open face 52 of the concavity 30 is substantially circular. The contact area provided by the open face 52 in this embodiment can thus be mathematically determined using the formula $\Pi(d/2)^2$, where d=the diameter of the concavity 30. The contact area provided by the open face 52 of the concavity increases the surface area over which a therapeutic agent can make contact with the inner surface of a body lumen. Residual within each concavity 30 can be a volume of fluid vehicle containing a therapeutic agent that establishes a concentration gradient of therapeutic agent as that agent closest to the inner surface of the body lumen is taken up into the tissues or is inactivated. Other mechanisms for drug dispersal are familiar within the relevant arts and depend upon the nature of the therapeutic agent and fluid vehicle under consideration. Increasing the volume of the concavity 30 can increase the amount of therapeutic agent available for contact with the tissues. The concavities 30 are adapted for containing within them fluids dispersed under pressure. Increasing the infusion pressure for the fluid within the concavity 30 can increase the penetration of the therapeutic agent into the luminal wall.

Figure 6:
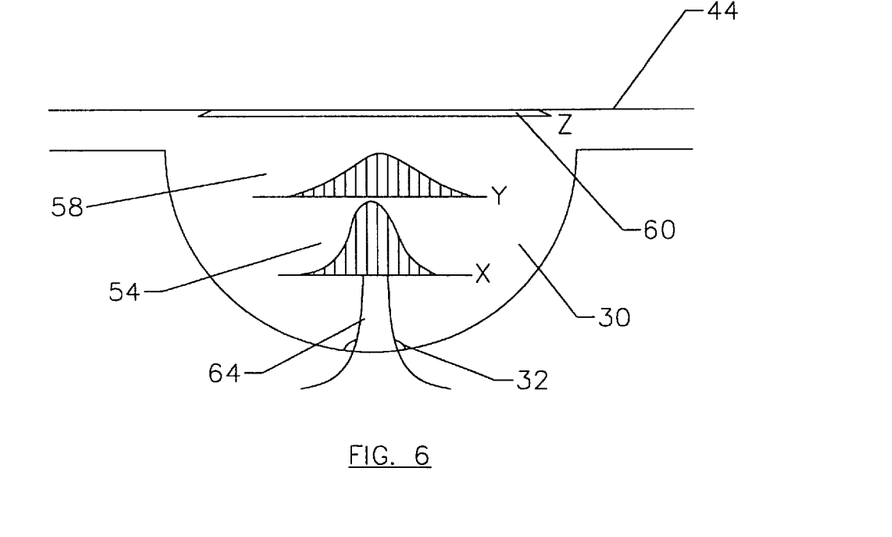
FIG. 6 is a cross-sectional view of a concavity in the balloon and depicts the change in the velocity wavepattern of the fluid being ejected through an aperture in the balloon wall.

FIG. 6 shows a schematic diagram of wave forms 54 and 58 of a fluid jet 64 exiting from the aperture 32 at the base of the concavity 30. Waveform 54 is sampled at distance X from the aperture 32, and waveform 58 is sampled at distance Y from the aperture 32, where Y>X. In the illustrated embodiment, the peak velocity of the fluid jet 64 is understood to be greater more proximal to the aperture 32, and the wave front 54 is more concentrated. As the fluid jet 64 moves away from the aperture 32 towards the interior surface 44 of the body lumen, its peak velocity decreases and its wave front disperses, as represented by the wave form diagram 58. These features of the fluid jet 64 permit the fluid vehicle to contact the interior surface 44 of the body lumen over a broader area of contact 60 with an attenuated velocity as compared to the velocity with which the fluid jet 64 exits the aperture 32. The area of contact 60 is at distance Z from the aperture 32 where distance Z is greater than distance Y. The preferred embodiment thereby minimizes the detrimental effects upon the interior surface 44 transmitted by the fluid jet 64 traveling at an excessive velocity and striking the interior surface 44 of the body lumen in a concentrated area.

Figures 7A, 7B:
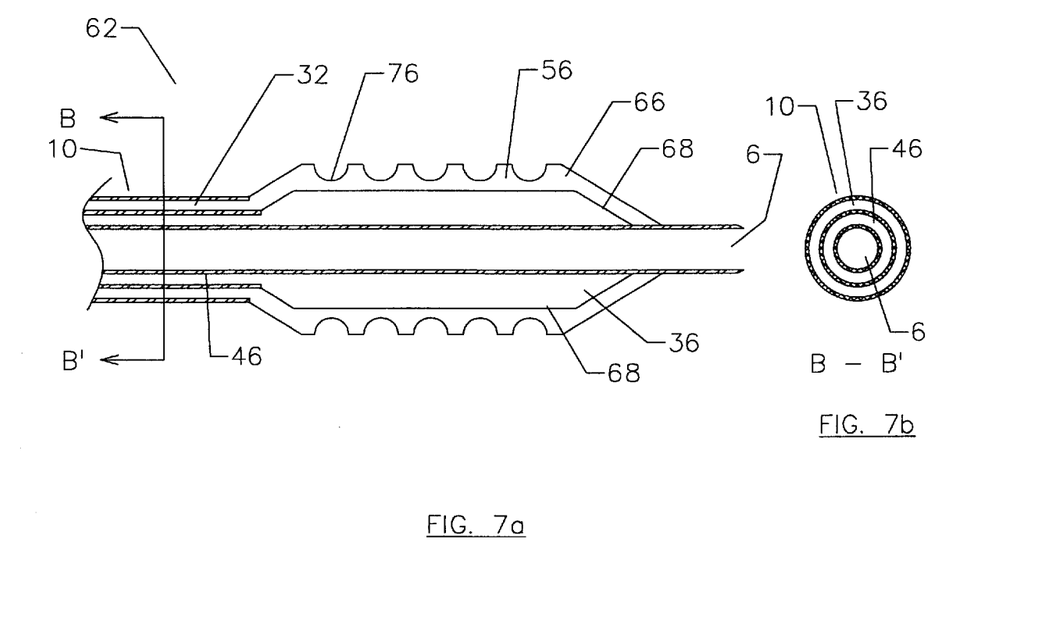

FIG. 7a shows an embodiment of a catheter system 62 wherein a dimpled porous balloon 66 is disposed on the distal end of a catheter 10 surrounding and external to an inner balloon 68. In this embodiment, the inner balloon 68 is depicted as being entirely surrounded by the dimpled porous balloon 66, although other arrangements of a plurality of balloons on the distal end of the catheter 10 are possible that fall within the scope of the systems disclosed herein. In this embodiment, the interior 56 of the dimpled porous balloon 66 is in fluid communication with the infusion lumen 36 contained within the catheter 10. The clinician is able to inject fluid through the infusion lumen 36 into the interior 56 of the dimpled porous balloon 66. At least one aperture 76 penetrates the wall of the dimpled porous balloon 66 to permit the egress of fluid from the interior 56. The interior 38 of the inner balloon 68 is in fluid communication with the inflation lumen 46 contained within the catheter 10. This embodiment is depicted with a guidewire channel 6 coaxial with and interior to the other depicted lumens. In this embodiment the infusion lumen 36 and the inflation lumen 46 are depicted as separate channels within the catheter 10, and are not shown as being in fluid communication with each other. However, these two lumens can be in fluid communication with each other or with additional lumens within the catheter 10 without departing from the scope of the systems disclosed herein. In this figure, no fluid communication between the interior 36 of the inner balloon 68 and the interior 56 of the dimpled porous balloon 66 is depicted. However, fluid communication between these two balloons, or between any other balloons can be provided without departing from the scope of the systems disclosed herein. Although this figure depicts the dimpled porous balloon 66 in relation to one inner balloon 68, a variety of arrangements of one or more inner balloons 68 are possible without departing from the scope of the systems disclosed herein. Furthermore, within the scope of these systems, alternative arrangements of balloons can be constructed wherein the dimpled porous balloon 66 is disposed proximal to, distal to or in between one or more balloons also disposed on the end of the catheter 10.

FIG. 7b depicts a cross-sectional view of the catheter 10 shown in FIG. 7a taken along line B–B'. This figure illustrates one coaxial arrangement of the lumens, wherein the guidewire channel 6 is the innermost, surrounded by the inflation lumen 46 for the inner balloon. In this figure, the inflation lumen 46 for the inner balloon is surrounded by the infusion balloon 36 for the dimpled porous balloon. It is understood that alternative arrangements of these lumens or of other lumens within the catheter 10 are possible without departing from the scope of the systems described herein.

Figure 8:
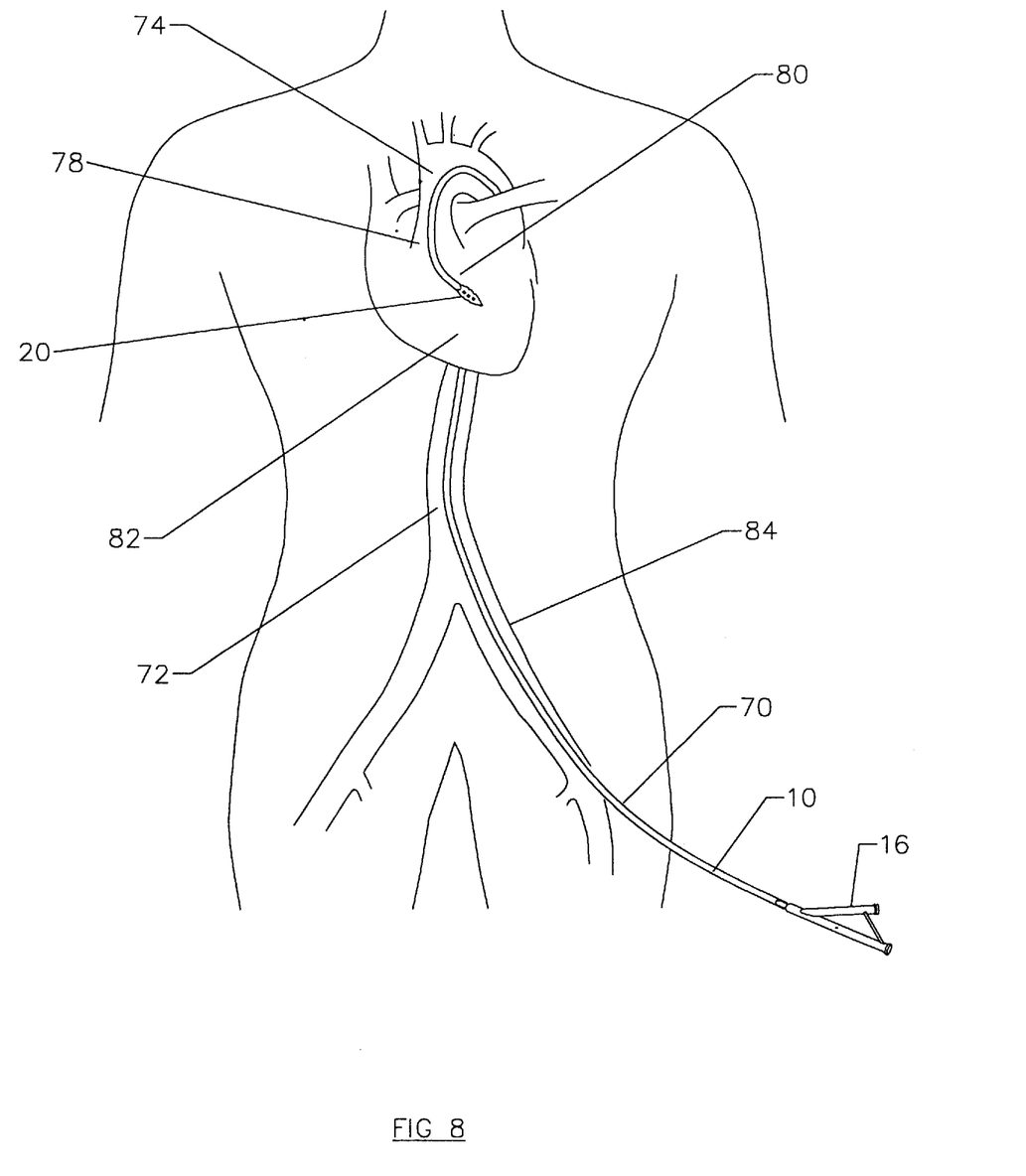
FIG. 8 is a schematic drawing of a patient with the catheter placed in accordance with a practice of the methods disclosed herein.

FIG. 8 is a diagram illustrating a method for the practice of the invention described herein. According to this practice, the catheter 10 bearing the balloon 20 is introduced into a body lumen, depicted in this Figure as a blood vessel 84. In the illustrated practice, vascular access 70 is accomplished in the standard way, either percutaneously or via cutdown. The catheter 10 is threaded into the descending aorta 72, through the ascending aorta 74 and into the aortic root 78. The catheter 10 is thereupon positioned within the coronary vessels 80. While the practice shown in this figure illustrates the adaptation of these methods to conditions affecting the heart 82, these methods can be extended readily to any blood vessel and to any body lumen without departing from the scope of the disclosed systems and methods. According to the practice depicted in this figure, the balloon 20, once positioned, is inflated to attain contact with the inner surface of the coronary vessel 80. Fluid is then infused through an infusion port 16 located on the proximal part of the catheter. The rate of infusion is selected by the clinician to provide delivery of the desired amount of a therapeutic agent to the targeted area. Once the intended amount of fluid has been delivered, the clinician deflates the balloon 20 and removes the catheter 10 from the blood vessel 84.

This method can be combined with techniques intended to dilate stenotic regions of a body lumen, or can be combined with other techniques to treat localized lesions of a body lumen. While an embodiment of these systems and methods that combines dilatation and drug delivery systems is directed towards blood vessels 84, alternative embodiments can be adapted for other body lumens without departing from the scope of the disclosed invention. Methods for treating stenotic regions of body lumens such as the endoluminal excision of a lesion producing a stenosis fall within the scope of the term dilatation as used herein. In the practice illustrated in FIG. 8, the treatment methods are directed towards blood vessels 84. According to this practice, these treatment methods can be combined with other techniques to treat localized blood vessel pathology. For example, a stenotic region of a blood vessel 84 can be stretched using the techniques of balloon dilatation and can be thereupon treated with the methods and systems described herein. As another example, drug delivery according to these methods and systems can be applied following procedures such as angioplasty, atherotomy, atherectomy and stent placement.

The systems and methods disclosed can provide treatment to any body lumen, and in one embodiment, these systems will be dimensionally adapted for disposition within a blood vessel. Blood vessels include both arteries and veins. Blood vessels range in size from large caliber like the aorta and the vena cava to small caliber like the coronary arteries. Blood vessels include areas of bifurcation and trifurcation where a single blood vessel branches into two or three vessels respectively. However, the uses of the disclosed systems and methods are not limited to blood vessels. Other pathological conditions exist wherein topical application of fluid vehicles containing therapeutic agents is desirable. Those skilled in the art will know or be able to ascertain using no more than routine experimentation many equivalents to the embodiments and practices described herein. For example, a tumor in the wall of a body cavity can be treated by the local application of antineoplastic agents, including chemotherapeutic agents and anti-angiogenic agents. The disclosed systems and methods will permit these agents to be directed against the inner surface of the body lumen and thereby gain access to the tumor. Yet another example of a pathological condition can be seen in esophageal varices, where the transesophageal topical application of sclerosing or thrombosing agents by the disclosed systems and methods can permit control of these lesions and their bleeding diatheses. A further example of a pathological condition is seen in post-traumatic or post-surgical cicatricial stenoses, where the systems and methods disclosed herein can provide for endoluminal application of a therapeutic agent to modify the properties of the scar tissue deposited or being deposited in the organ wall.

It will be understood to those of ordinary skill in the art that the systems and methods described herein provide advantages over the prior art including a larger surface area for drug delivery and a diminishing of the damaging effects of fluid jetting upon luminal walls. The systems and methods herein described provide these advantages in addition to the advantages inherent in localizing the delivery of therapeutic agents to targeted tissues.

Accordingly, it will be understood that the invention is not to be limited to the embodiments disclosed herein, but is to be understood from the following claims, which are to be interpreted as broadly as allowed under the law.

I claim:

1. Apparatus for applying a fluid vehicle carrying a therapeutic agent to an interior surface of a body lumen, comprising:

a catheter having a distal portion, a proximal portion and a lumen therethrough; and a balloon mounted on the distal portion of the catheter having an interior in fluid communication with the lumen of the catheter and having a wall capable of being expanded within the body lumen to contact the interior surface of the body lumen, said wall being penetrated by at least one aperture situated within a concavity in the wall of the balloon;

whereby the therapeutic agent can be delivered from the interior of the balloon through the aperture in the wall of the balloon to contact the interior surface of the body lumen.

2. Apparatus according to claim 1 wherein the wall of the balloon bears a plurality of concavities, each of said concavities containing within it at least one aperture adapted for permitting the egress of the fluid vehicle carrying the therapeutic agent.

3. Apparatus according to claim 1 wherein the concavity in the wall of the balloon spaces the aperture away from the tissue wall for decreasing the velocity at which the fluid vehicle carrying the therapeutic agent contacts the interior surface of the body lumen.

4. Apparatus according to claim 1 wherein the concavity in the wall of the balloon permits accumulation of the fluid vehicle under pressure.

5. Apparatus according to claim wherein the concavity is substantially hemispherical.

6. Apparatus according to claim 2 wherein each concavity is penetrated substantially at its base by at least one aperture.

7. Apparatus according to claim 1 wherein the catheter and the balloon are dimensionally adapted to be disposed within a blood vessel.

8. Apparatus for applying a fluid vehicle carrying a therapeutic agent to an interior surface of a body lumen, comprising:

a catheter having a distal portion and a proximal portion and a lumen therethrough; and a first balloon mounted on said distal portion of the catheter having an interior in fluid communication with the lumen of the catheter and having a wall capable of being expanded within the body lumen to contact the interior surface of the body lumen, said wall being indented by a plurality of concavities, each of said concavities being penetrated by at least one aperture permitting egress of the fluid vehicle carrying the therapeutic agent;

wherein the concavities in the wall of the balloon distance the apertures in the wall from the interior surface of the body lumen and accumulate the therapeutic agent within the concavities, thereby bringing the therapeutic agent into contact with the interior surface of the body lumen.

9. Apparatus according to claim 8, wherein the concavities are substantially hemispherical.

10. Apparatus according to claim 8, wherein at least one aperture is situated substantially at the base of each concavity.

11. Apparatus according to claim 8, wherein the catheter and the balloon are dimensionally adapted to be disposed within a blood vessel.

12. Apparatus according to claim 8, wherein at least one additional balloon is mounted on the distal portion of the catheter.

13. Apparatus according to claim 12 wherein the first balloon is disposed exterior to and coaxial with at least one additional balloon.

14. Apparatus according to claim 12, wherein at least one additional balloon is a dilating balloon adapted for the dilatation of a stenosis of a body lumen.

15. A method for applying at therapeutic agent to an interior surface of a body lumen, comprising:

providing a catheter having a distal portion and a proximal portion and a lumen therethrough, a balloon disposed on the distal portion of the catheter with an interior in fluid communication with the lumen of the catheter and with a wall having a plurality of apertures and a plurality of concavities each bearing at least one aperture, a means for inflating the balloon and a means for directing a fluid vehicle carrying the therapeutic agent through the inner lumen of the catheter to the interior of the balloon;

inserting the catheter into a patient;

positioning the balloon within the body lumen;

inflating the balloon in the body lumen to attain contact with the inner surface of the body lumen;

maintaining a level of fluid pressure in the balloon so that the fluid vehicle carrying the therapeutic agent extravasates through the perforations in the wall at a flow rate selected to deliver a desired quantity of the therapeutic agent to the inner surface of the body lumen;

deflating the balloon; and removing the catheter from the body lumen.

16. A method according to claim 15 including dilating a stenotic region of the body lumen.

* * * * *

UNITED STATES PATENT AND TRADEMARK OFFICE
CERTIFICATE OF CORRECTION

PATENT NO. : 6,048,332

DATED : April 11, 2000

INVENTORS : Duffy *et al.*

It is certified that an error appears in the above-identified patent and that said Letters Patent is hereby corrected as shown below.

In column 3, line 28, "5,242,158" should be --5,217,434--.

In column 13, line 31, insert --1-- after "claim".

In column 14, line 24, "at" should be --a--.

Signed and Sealed this

Twenty-seventh Day of March, 2001

*Attest:*

NICHOLAS P. GODICI

*Attesting Officer*

*Acting Director of the United States Patent and Trademark Office*